United States Patent [19]

Landau

[11] 3,976,886

[45] Aug. 24, 1976

[54] APPARATUS FOR EFFECTING A SIMULTANEOUS MULTIPLE TOMOGRAPHY

[76] Inventor: Pierre Landau, 62 bis, Rue de la Tour, 75016 Paris, France

[22] Filed: Nov. 6, 1975

[21] Appl. No.: 629,675

[30] Foreign Application Priority Data

Nov. 18, 1974  France .............................. 74.37876

[52] U.S. Cl. .............................. 250/445 T; 250/468
[51] Int. Cl.² ......................................... G03B 41/16
[58] Field of Search ......................... 250/445 T, 468

[56] References Cited
UNITED STATES PATENTS 3,291,983  12/1966  Landau ........................... 250/445 T

*Primary Examiner*—Craig E. Church
*Attorney, Agent, or Firm*—Robert E. Burns; Emmanuel J. Lobato; Bruce L. Adams

[57] ABSTRACT

In order to impart to film-screens assemblies homothetic relative sliding with respect to each other which are required for obtaining six tomographic sections, the upper film-screen assembly support is coupled to a driving spring whose end is connected to a transmission leading to the input member of a regulating device. The latter is constituted by two single-acting jacks whose chambers intercommunicate, in the direction of the travel for operation of the apparatus, through an adjustable constriction and, in the return direction, through a check-valve. In the armed position, the rod of one of the jacks, is retained by a locking device. The travel of the film-screens assemblies corresponding to the tomographic sweep, is initiated by the emission of X-rays through the electromagnet. The return travel, which places the apparatus in the armed position, is ensured by means of a key constituting a winding means. The constant speed of displacement of the films is regulated by a knob and a selector knob regulates the symmetry.

23 Claims, 8 Drawing Figures

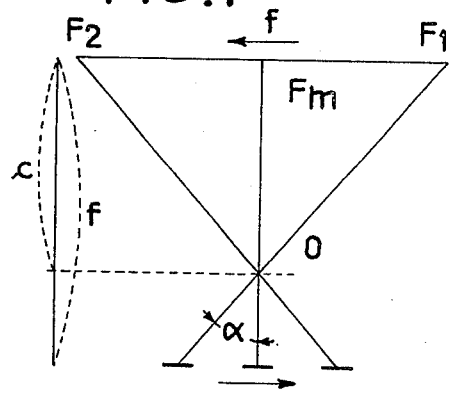
FIG. 1
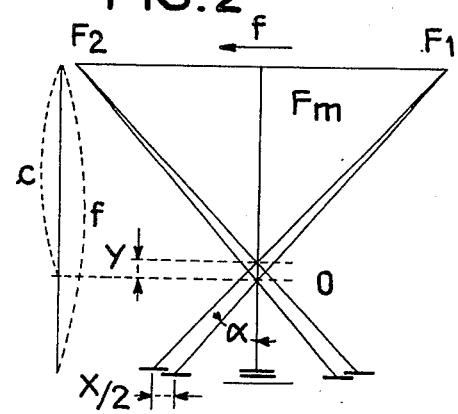
FIG. 2
FIG. 3
TABLE OF SPEEDS
FOR A SWEEP ANGLE OF 30°
| EXPOSURE TIME | SPACING BETWEEN SECTIONS (cm) | | | |
|---|---|---|---|---|
| | 0.5 | 1 | 1.5 | 2 |
| 1 sec. | 1.5 | 3 | 4.5 | 6 |
| 2 sec. | 0.75 | 1.5 | 2.25 | 3 |
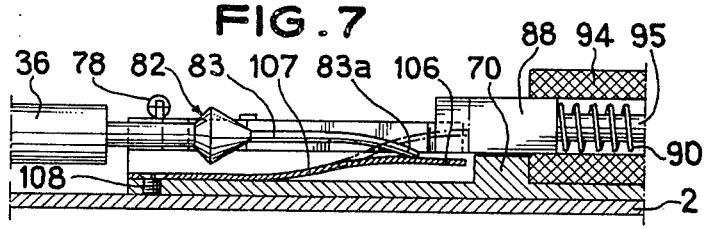
FIG. 7
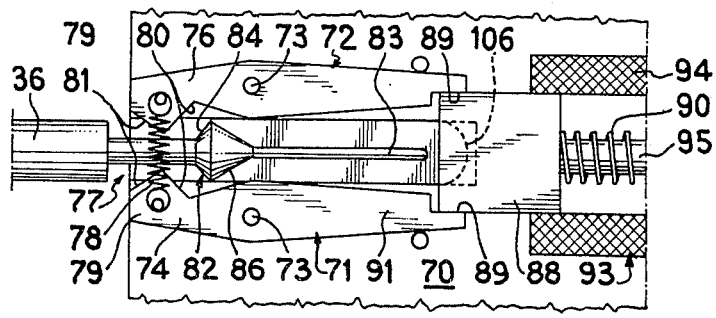
FIG. 8

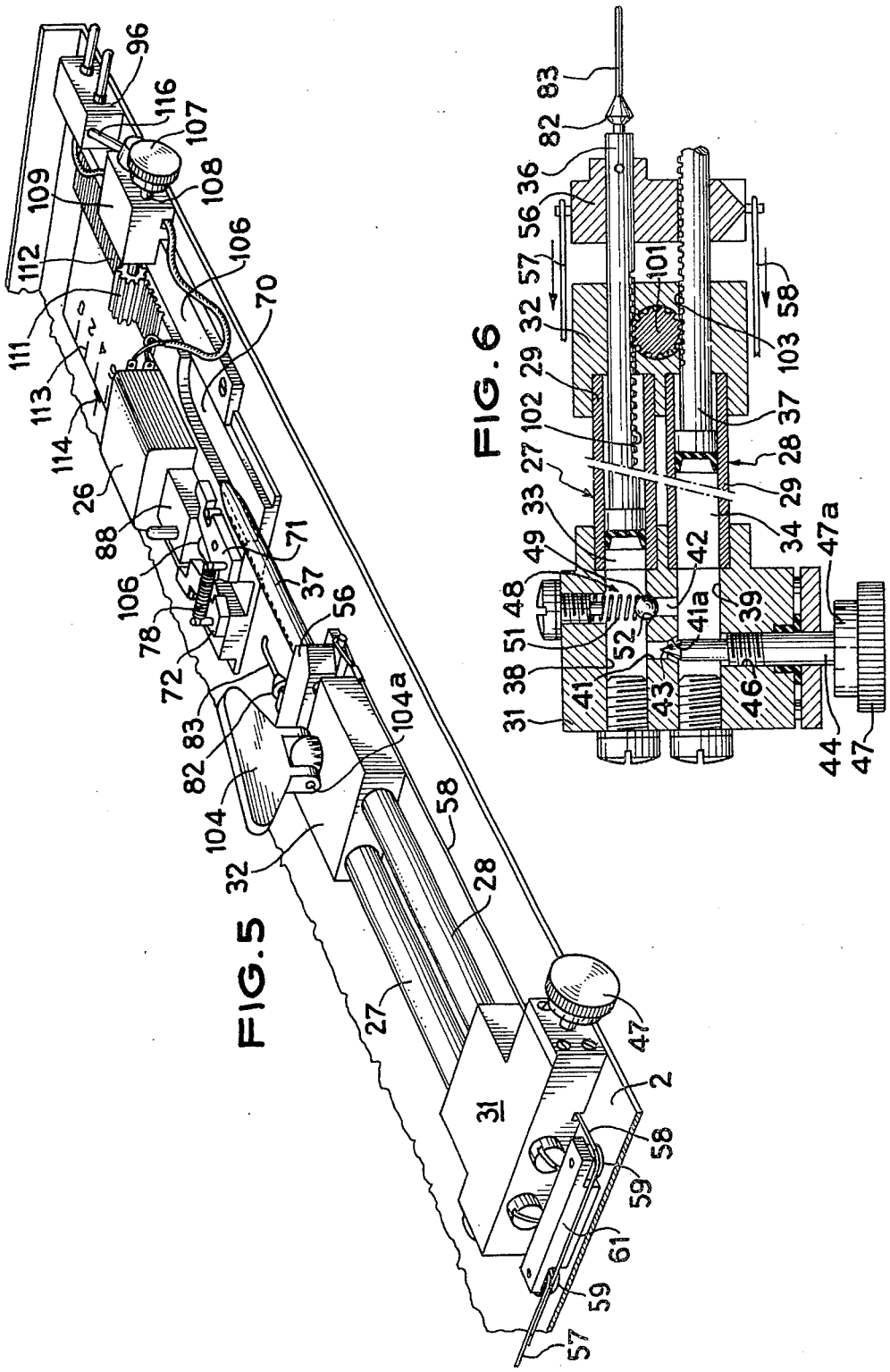

APPARATUS FOR EFFECTING A SIMULTANEOUS MULTIPLE TOMOGRAPHY

The present invention relates to an apparatus for effecting a simultaneous multiple tomography comprising inside a cassette adapted to be inserted in a case having an anti-diffusion grid, or Potter, of the table of a radiologic unit a stack of thin assemblies comprising a film and reinforcing screens coupled with each other by at least one pivotal arm on which there are pivoted supports which are preferably in the form of a strip and are connected to the respective assemblies, the arm being constrained to effect, during the rectilinear travel of the Potter which is synchronized with the sweeping travel of the radiogenic source, an angular movement under the effect of which the film-screens assemblies undergo relative rectilinear displacements which are proportional to the displacement of the Potter with respect to the table.

It its usual form, this apparatus which is disclosed in U.S. Pat. No. 3,291,983 permits—in the course of a general movement of the Potter giving on a first fixed film, inserted in a pair of reinforcing screens, a tomographic section termed the base section—obtaining simultaneously five other tomographic sections on subjacent films each inserted in a pair of screens, the six film-screens assemblies sliding with respect to each other in accordance with different displacements which are all homothetic. All these movements are produced by the tomographic movement itself owing to a mechanical connection between one of the arms of a control lever whose other arm is constituted by the pivotal arm connected to the assemblies and a finger member fixed to the radiologic table (see French Patent No. 1,336,114 and U.S. Pat. No. 3,291,983 and the French "Journal de Radiologie" of November 1962, page 788).

The known apparatus, apart from the fact that it gives pictures of good quality irrespective of the distance between the sections owing to the proximity of the films and the anti-diffusion grid, can be easily employed in the most common vertical or horizontal linear tomograph units which are of relatively simple construction.

During the last ten years, there have developed, above all in France, the image intensifier and remost control which have afforded the operator a protection against radiations but above all an absolutely remarkable facility and comfort as concerns working conditions.

Although these remote-controlled radiologic tables (which are extremely complicated and costly) offer the user multiple possibilities they preclude the utilisation of the known apparatus in its present version owing to the complexity of the remote-controlled units and more particularly because it is absolutely impossible to establish the necessary mechanical connection with the radiologic table.

It is true that unidirectional tomograph units which equip the remote-controlled tables are equipped with very ingenious electronic devices which program the required tomographic section and, here again, greatly facilitate the work of the operator. But these electronic devices do not eliminate the major drawback of the simple tomographic method, namely the magnitude of the dose delivered to the patient, which necessitates limiting the tomographic sections in the child, the pregnant woman or subjects professionally exposed to ionizing radiations.

Moreover, it seems illogical to effect successive sections, even close to each other with respect to time, when using artificial contrasts giving transitory images (nephrotomography, arteriography in section).

The following paradoxical situation is reached: simple radiologic tables of old design can benefit from simultaneous multiple tomography which is impossible with modern remote-controlled tables apart from a few exceptions (simultaneous tomographies of the otic bone in which the very small distance between the sections permits the use of the "book cassette" whose drawbacks are well known).

An object of the invention is therefore to provide an apparatus of the aforementioned type in which the relative sliding movements of the film-screens assemblies in accordance with a homothetic or proportionality law can be obtained with no mechanical connection between the radiologic table and the parts located inside the cassette.

According to the invention, there is provided an apparatus comprising:

a driving device coupled to one of the supports, or pilot-support, and capable of imparting to the pilot - support a rectilinear travel at constant speed between an initial position and a final position, a locking device which retains in its operative position the support in its initial position to which the driving device is coupled, and an actuating device controlled by the movement of the radiogenic source and cooperating with the locking device in such manner that the moment when, during the tomographic sweep travel, the emission of the X-rays starts, the locking device is rendered inoperative and the pilot-support is released, so that under the effect of the driving device the film-screens assemblies effect the required relative differential travels.

In order to ensure that the condition of proportionality or homothety be achieved in the proposed cassette, it is necessary that the rectilinear displacement of the radiogenic source and the cassette be, in the same way as the displacement of the movable film-screens assemblies, effected practically at constant speed so that the distances that each moving element travels through in equal intervals of time be equal. The constant speed of the radiogenic source is obtained with certainty in the modern remote-controlled units — to which the invention is particularly applicable — whose geometric and kinematic data are defined in a precise manner. This constancy of the speed can be obtained also in old radiologic units of simple construction on condition that suitable means are provided for the translation of the radiogenic source.

As the condition of proportionality is satisfied, the required tomographic sections are obtained with no mechanical connection between the cassette and the other parts of the radiologic unit. The control of the actuating device by the radiogenic source constitutes a non-mechanical connection which is preferably achieved by an electrical connection which is much easier to achieve than the kinematic cooperation of the known apparatus.

This non-mechanical connection can obviously be in other forms and employ for example photoelectric cells placed behind the stack of film-screens assemblies and combined with transistorized amplifying devices to produce the actuation of the driving device under the effect of the emission of X-rays.

In a preferred embodiment, the driving device comprises an extensible elastically yieldable element constituted for example by a constantly tensioned tension coil spring which exerts on the pilot-support a force in the direction of the working travel and is connected through a cable or wire transmission to a regulating mechanism capable of imparting a constant-speed displacement to the active end of the driving element.

According to another feature of the invention, the regulating mechanism comprises two single-acting hydraulic jacks whose work chambers are connected to each other through two conduits disposed in parallel, one of which conduits comprises an adjustable constriction whereas the other is controlled by a check valve which is closed when the pressure is exerted in one of the jacks, considered as the primary jack, whose rod is subjected to the action of the transmission and cooperates with the locking device. This cooperation is such that, in its operative position, the locking device retains the rod of the primary jack in the initial armed position in which the spring is put under full tension and is ready to be released to undergo a working travel which becomes effective, at the moment when the actuating device places the locking device in the inoperative position, by releasing the rod of the primary jack which, under the effect of the pull exerted by the transmission, causes the hydraulic liquid to travel through the adjustable constriction in accordance with a predetermined rate of flow and fill the work chamber of the other jack, or secondary jack, while performing the required regulating function.

The locking device is normally maintained in its operative position by a movable locking member which is part of the actuating device and is, on one hand, resiliently yieldably biased to the position in which it maintains the locking device in its locked operative position and, on the other hand, integral with the plunger of an electromagnet the energizing of which, produced by the emission of X-rays from the radiogenic source, unlocks the locking device.

The locking device may be constructed in the form of two pivoted pawls which, on one side of the pivot pins, form the branches of a jaw capable of retaining in the initial armed position the rod of the primary jack by closing under the effect of a spring onto anchoring means forming a profiled enlargement which is capable of separating the branches, in opposition to the action of the spring, when the locking member is in its inoperative position, under the effect of the displacement, in one direction or the other, of the rod of the primary jack.

In order to permit the re-arming of the assembly comprising the driving spring and the regulating device or after a tomographic sweeping travel has been effected, the parallel rods of the two jacks support racks which are kinematically coupled in opposite directions by means of a gear pinion integral with a rotary shaft on which there is fixed a control means, the rotation of the latter in the desired direction ensuring the return of the rod of the primary jack to the initial position and causing the flow of the fluid from the secondary jack to the primary jack through the open check-valve.

In order that the same zone of the tomographed subject appears in the different sections, in homologous zones, it is necessary that the initial position and final position of each film be symmetrical with respect to the same main plane perpendicular to the direction of translation of the films and which, in the general case of a single pivotal arm, passes through the pivot axis of this arm. Therefore, the films must be given a definite initial position which corresponds to the half total rectilinear travel which will be imparted thereto and which may vary for each exploration in accordance with the distance between the sections. For this purpose, the locking device is carried by a mount which is capable of sliding on the cassette in the direction of displacement of the rod of the primary jack so that the initial armed position of the primary jack rod, and consequently the initial position of the pilot-support, which are defined by the position occupied by the jaw of the locking device, can be fixed as desired. This adjustment of position can be achieved by rotating a selecting means acting on the mount through a rack and pinion mechanism. It is advantageous in this respect that the initial positions of the pilot-support be capable of being read off a scale marked on an edge of the sliding mount in front of an index on the cassette. For each exploration, this regulation of symmetry must be carried out jointly with a regulation, by means of a needle valve member, of the constriction through which the hydraulic liquid flows during the working travel for determining the distance between the sections.

The constructional arrangements of the apparatus according to the invention permit housing all of its elements in a cassette of standard format whose thickness does not exceed 16 mm.

The invention will be explained in the ensuing description with reference to the accompanying drawings, in which:

FIG. 1 is a diagram of the principle of operation of a simple tomographic section;

FIG. 2 is a diagram of a multiple tomographic section obtained by a relative sliding of two films;

FIG. 3 is a table giving the speeds of a reference film as a function of the exposure time and the spacing of the sections;

FIG. 5 is a perspective view to an enlarged scale of the regulating mechanism, the locking device and the actuating device;

FIG. 6 is a sectional view through the jacks which are part of the regulating mechanism;

FIG. 7 is a vertical sectional view of the locking device in the armed position, and FIG. 8 is a corresponding plan view of the device shown in FIG. 7.

Figure 4:
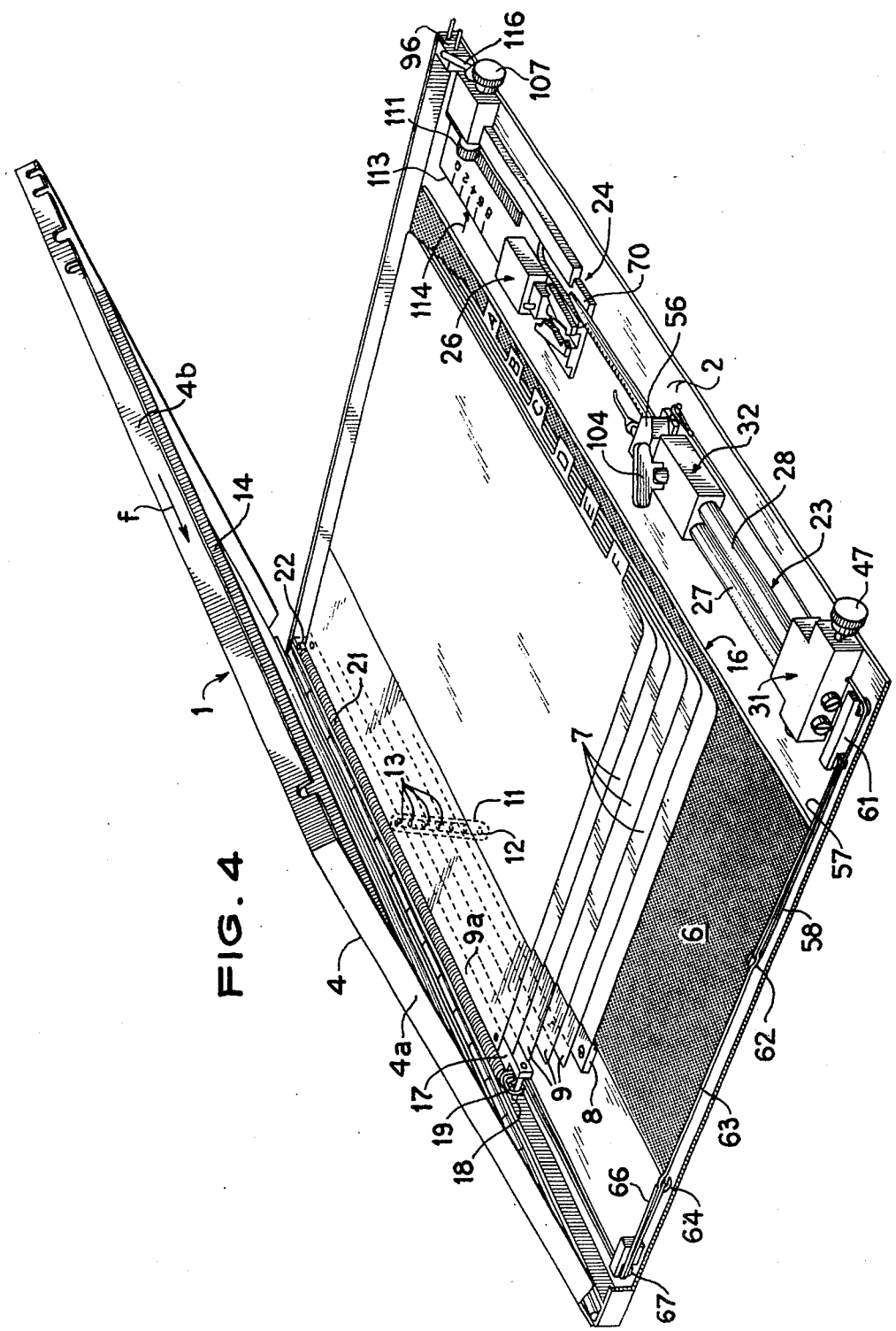
FIG. 4 is a perspective view of a simultaneous multiple tomography apparatus.

In FIG. 1 which shows a tomographic section, the following notations have been adopted:

$f$: distance between the rectilinear path $F_1$, $F_2$ of the radiogenic source F and the plane of the film A, $c$: distance between the radiogenic source and the plane of the section, $2\alpha$: sweep angle, $t$: duration of the irradiation or exposure time.

The angular velocity of the sweep is constant and has for value $2\alpha/t$.

The linear velocity of the film may be considered as constant for $\alpha \leqslant 15°$, that is to say for a sweep angle equal to or less than 30°, and has for value $2(f-c)\tan\alpha/t$.

In FIG. 2, which represents two simultaneous tomographic sections effected in accordance with the teaching of French Patent No. 1,336,114, the lower film A is fixed in the cassette; the base section of the tomograph corresponds thereto. The film B above the film A slides on the latter in a movement which is homothetic to the tomographic sweep. An examination of FIG. 2 will immediately show the symmetry of the initial and final relative positions of the films A and B with respect to a main plane ZZ passing through the centre of homothety. This notion of symmetry is very important and has for advantageous consequence that an opacity visible on a plurality of simultaneous sections appears on homologous zones of the surface of the films, for example central zone of the films.

This symmetry is achieved automatically in the known apparatus owing to the kinematic coupling between the radiogenic source, whose travel is symmetrical, and the stack of film-screens assemblies, but will have to be achieved, in the apparatus according to the invention, by a special regulation for each exploration.

If $x$ designates the total displacement of the film B with respect to the film A, $y$ the spacing between the sections A and B, calculation, developed in the aforementioned patent, gives the following relation:

$$y = \frac{cx}{2f \tan \alpha} \quad (1)$$

This approximate relation, which is perfectly valid in practice, takes into account the fact that the surfaces of the films are not coincident.

It results from (1) that the interval or spacing between the sections, corresponding to two films, is proportional to the relative displacement of one of these films with respect to the other.

From the relation (1) there is derived:

$$x = \frac{2fy \tan \alpha}{c}$$

Assuming that the stack comprises, not two films but six, giving six simultaneous sections designated by the letters A, B, C, D, E, F, the section A being the base section, the displacement of the film F is equal to:

$$5x = \frac{10 fy \tan \alpha}{c}$$

and the speed of displacement of this film with respect to the cassette, that is to say with respect to the film A, is equal to:

$$\frac{10 fy \tan \alpha}{ct}$$

With these data it is possible to draw up a table of the displacements of the film F for a given distance $f$ and for a spacing of base section of 1 cm as a function of the height of the section and of the angle of sweep. This table permits determining the displacement to be imparted to the film F for any section spacing by multiplying the values of the table by the magnitude of the spacing.

The speed of the film F is then obtained by dividing its displacement by the exposure time.

In practice, it is simpler not to take into account the variable height of the base section by adopting for this height a value of 6 cm, the error between the section spacing being minimum. By fixing the sweep angle at 30°, the simplified table shown in FIG. 3 is obtained which has been established for $f = 107$ cm.

The principles just mentioned are employed in the simultaneous multiple tomography apparatus shown in FIG. 4. This apparatus comprises a cassette 1 having a bottom wall 2 on one of the longitudinal edges of which a cover 4 is pivoted at 3. This cassette is adapted to be inserted in the case having an anti-diffusion grid, or Potter, of the table of a radiologic unit. Bearing in mind present standardized dimensions, this cassette is thin when closed, the thickness being of the order for example of 16 mm. In the centre part of the bottom wall 2, there is provided a layer 6 of felt which supports a stack of six pairs of reinforcing screens of plastics material 7 carrying reference letters A, B, C, D, E, F, respectively, provided for undergoing a relative sliding motion in the longitudinal direction of the cassette so as to obtain six tomographic sections on six films engaged between respective pairs of screens. For this purpose, each pair of screens 7 is fixed by an adhesive band to a strip which is fixed to a support in the form of a bar which extends in the direction of translation of the pairs of screens. The lower bar 8 is fixed to the bottom wall of the cassette between the edge of the felt layer 6 and the hinge 3. The other bars 9 are transversely offset toward the hinge 3 and are in mutual sliding contact while being kinematically coupled by an arm 11 which is pivoted at 12 to the bottom wall of the cassette 2 and to which each bar is pivoted in the middle of the bar by a pin 13. In the closed position of the cover 4, the sealing with respect to light is ensured by the lateral flanges 4a of the cover and, further, by a rib or L-section member 14 disposed longitudinally at a distance from the longitudinal edge 4b of the cover, this rib coming in contact with the felt layer 6 along the line 16.

In order to impart to the film-screens assemblies A to F relative sliding movements which are homothetic with respect to each other, required for obtaining the six sections, the bar 9a supporting the uppermost film-screens assembly F constitutes a pilot-bar and is provided at one end with a member 17 whose free end carries a transverses rod 18 on which there is hooked one of the ends 19 of a tensile coil spring 21 which is constantly under tension, the other end 22 of the spring being fixed to the bottom wall of the cassette 3. The spring 21 is a driving spring whose extension is subjected to the action of a regulating device 23 which is associated with a locking and arming device 24 associated with an actuating device 26. These three devices are disposed in alignment on the bottom wall of the cassette 2 in a region between the longitudinal edge of the cassette opposed to the hinge 3 and the stack of film-screens assemblies.

The regulating device 22, whose function is to impart to the end 19 of the spring 21 a driving travel at constant speed, comprises two single-acting jacks 27, 28 (FIGS. 5 and 6) which are in side-by-side relation parallel to the longitudinal edges of the cassette. The jack bodies 29 extend between two blocks 31, 32 fixed to the bottom wall of the cassette 2 which respectively serve to transfer the hydraulic liquid from one work chamber 33 to the other work chamber 34 of the jacks and to guide the rods 36, 37 of these jacks. For this purpose, the work chambers 33, 34 are extended in the block 31 by bores 38, 39 one of which communicates with the other by way of radial orifices 41, 42. The orifice 41 comprises, adjacent the bore 29, a conical portion 41a which constitutes an adjustable constriction in combination with the end, constituting a needle valve member 43, of a screwthreaded rod 44 which is screwed at 46 in a transverse bore in the block 31 and provided with an actuating knob or wheel which is accessible outside the closed cassette. The orifice 42 is controlled by a check-valve 48 whose ball 49 is biased by a spring 51 in contact with a seat 52 adjacent the bore 38 associated with the work chamber 33 of the jack 37. The latter is a primary jack whose rod 36 is fixed to a cross-member 56 at the ends of which there are fixed by their corresponding ends two portions of cable 57, 58 which extend from the cross-member 56 in a direction parallel to the rods of the jacks and then undergo, after having extended through the block 31, a change in direction of 90° by extending around two pulleys 59 mounted on a member 61 fixed to the bottom wall of the cassette 2. The two cable portions 57, 58 form at their end opposed to the cross-member 56 a loop engaged on a hook 62 formed at one end of a rod 63 whose other end 64 is connected by a cable 66, which extends around a pulley 67 and changes direction at 90°, to the member 17 attached to the end of the bar 9a.

The locking device 24 retains the rod 36 of the primary jack, and consequently the bar 9a, in an initial armed position in opposition to the force exerted by the spring 21 through the transmission comprising the cable 66, the rod 63 and the cable portions 57, 58. This locking device (FIGS. 7 and 8) comprises two twin pawls 71, 72 which are pivoted by pins 73 to a plate 70 slidably mounted on the bottom wall of the cassette 2. On the side of the pivot pin 73 adjacent the jacks 27, 28 the pawls form branches 74, 76 of a jaw 77 capable of closing, under the action of a tension spring 78 interconnecting the two branches, so as to trap between the two nose portions 79, having a triangular shape 80, 81, a biconical enlargement 82 carried by a rod 83 extending the rod of the jack 36. The surfaces 84, 86 of the enlargement 82 constitute cams which respectively cooperate with the faces 80, 81 of the pawl nose portions 79 so as to move apart the branches 74, 76 of the jaws when the jack rod 36 retracts or extends with respect to the jack 27. In the armed position shown in FIGS. 7 and 8, the separating movement or opening movement of the jaw 77 is prevented owing to the fact that a locking means 88, which is part of the actuating device, is inserted in a passageway 89 formed between the two arms 91, 92 of the pawls 71, 72 which extend on the opposite side of the pivot pin 73 to the jaw branches. The opening of the jaw 77, which permits, starting at the shown armed position, the release of the jack rod 36 and the initiation under the action of the spring 21 of the differential travels of the film-screens assemblies, is only possible if the locking means 88 is moved out of its illustrated operative position in opposition to the action of the spring 90. For this purpose, the locking means 88 is integral with a plunger 95 of an electromagnet 93 carried by the plate 70 whose coil 94 is connected in a circuit by means of an electric plug 96 (FIGS. 4 and 5), the supply of current thereto being controlled by the emission of the radiations of the radiogenic source of the radiographic unit so that the relative sliding movement of the film-screens assemblies is synchronized with the tomographic sweep travel of the radiogenic source effected at constant speed.

In FIGS. 7 and 8 the biconical enlargement 82 which serves to retain the jack rod 36 in the jaw 37, is out of contact with the nose portions 79. This is due to the fact that the thrust exerted by the cable portions 57, 58 on the rod 36 is neutralized by the hydraulic liquid contained in the work chamber 33 and in the bore 38 which cannot escape through the orifice 41, closed by the needle valve member 43, nor through the orifice 43 closed by the ball 49. The jack rod 36 is therefore held stationary and can only be moved under the effect of the actuating device 26 (by retraction of the locking means 88) by first unscrewing the screwthreaded rod 44 which permits a flow of the hydraulic liquid between the chamber 38 of the primary jack and the chamber 39 of the secondary jack whose rod 37 then travels outwardly of its jack body. This flow occurs in accordance with a rate of flow determined by the extent to which the control knob 47 is turned (FIG. 6), this rate of flow determining the constant speed at which the pilot-bar 9a (FIG. 4) is driven. This speed, on which the spacing between the tomographic sections depends and which was mentioned hereinbefore with reference to FIGS. 2 and 3, may be read off from a scale 47a marked on the regulating knob 47.

When the rod 36 has terminated its return travel, and the film-screens assemblies have undergone the required relative displacements, the system formed by the driving spring 21 and the regulating device must be returned from the final position to the initial armed position. For this purpose, the two jack rods 36, 37 are coupled by a gear pinion 101 which is journalled in the block 32 and meshes with two racks 102, 103 formed on the rods and there is provided an arming key 104 integral with the pinion 101 the clockwise rotation of which (FIG. 6), after the needle valve member 43 has closed the orifice 41, causes the jack rod 37 to retract into its jack body whose effect is to urge the liquid back through the check-valve 48 and cause the rod 36 of the primary jack to extend out of the body 29. This extension travel is effected while the locking means 88 of the actuating device is retained in the inoperative or withdrawn position thereof shown in FIG. 5 in full line, and in FIG. 7 in dot-dash line, in opposition to the action of the spring 90, by a withdrawable stop 106 constituted by the upwardly deformed end portion of an elastically yieldable strip 107 fixed at 108 to the plate 70 (FIG. 7). The jaw 77 can therefore open at the moment when the conical surface 86 of the enlargment 82 of the rod 83 engages the surface 81 of the nose portions 79, and thereafter close under the effect of the spring 78. However, at the end of the extension travel of the jack rod 36, the jaw is locked in the closed position owing to the withdrawal of the stop 106 under the action of vertical pressure exerted on this stop by a downwardly bent end portion 83a of the rod 83 extending the jack rod 36 so that the locking means is disposed in the passageway 89 in its operative position under the effect of the spring 90.

The arming key 104 advantageously comprises a pivot pin 104a which enables it to be swung back against the top side of the block 32 after it has been actuated. In its position of use shown in FIGS. 4 and 5, this key projects through an opening of the cover 4.

In order to permit a regulation of the initial position of the pilot-bar 9a for ensuring, bearing in mind the total displacement established from the table shown in FIG. 3, that the initial and final positions are symmetrical, the plate 70 supporting the locking device 24 and the actuating device 26 may be moved in translation longitudinally of the cassette in contact with a slideway 106 by means of a selector knob 107 mounted on a shaft 108 which is journalled in a block 109, fixed to the bottom wall of the cassette 2, and carries at its opposite end a gear pinion 111 meshed with a rack 112 carried by the plate 70. Adjacent the edge of the plate 70 opposed to the rack 112, the plate has a scale 113 which gives the length of the total travel of the pilot-bar 9a and is in front of an index 114 marked on the bottom wall of the cassette. This graduation is of course established to the scale of one-half. The lever 116 controls a brake whereby it is possible to stop the shaft 108 and the plate 70 in the position defined by the setting of the selector means or knob 107.

In the present description and the accompanying claims, "final position" refers to the situation of the system corresponding to the ceasing of the emission of the X-rays in the course of the tomographic sweep. The arrangement of the apparatus is such that by means of a prior adjustment of the sliding plate, this final position must be symmetrical with the initial position with respect to the main plane perpendicular to the direction of travel and containing the pivot pin 12 of the arm 11. The final position thus defined is not determined mechanically since, after the end of the emission of the X-rays, the film-screens assemblies continue their travel to an end position of abutment which is fixed and embodied by a stop member (not shown) fixed to the bottom wall of the cassette.

Note moreover that the description and the drawings have been made on the assumption that the tomographic sweep of the radiogenic source is horizontal and travels from the right to the left when viewed from in front of the opening of the Potter (direction of arrow f in FIG. 4). In respect of a sweep which would be from the left to the right, the cassette described hereinbefore could be employed after rotation thereof, through 180° in its plane so that it is introduced by its opening side and not by its hinge side. In this case, a second electric plug mounted in parallel with the first-mentioned plug 96 and located adjacent the hinge would be employed.

Everything that has been mentioned with reference to the horizontal tomography can be transposed to the vertical tomography in which it is possible to obtain an upward or downward sweep. In all cases the apparatus must be introduced in the Potter in such manner that the arrow f shown in FIG. 4 is pointing in the direction of the tomographic sweep.

Having now described my invention what I claim as new and desire to secure by Letters Patent is:

1. In a simultaneous multiple tomography apparatus comprising a cassette adapted to be inserted in a case having a anti-diffusion grid, or Potter, of a table of a radiologic unit, and, disposed inside the cassette, a stack of thin assemblies of films and reinforcing screens, a lever pivotable relative to the cassette, each film-screens assembly having connected thereto a support, the pivotal lever being pivoted to the supports to interconnect the supports, the lever being capable of effecting, under the effect of a rectilinear travel of the Potter which is synchronized with a sweep travel of a radiogenic source of the radiolic unit, an angular movement under the effect of which movement the film-screens assemblies undergo relative rectilinear travels proportional to the travel of the Potter relative to the table; the improvement comprising:
   a driving device connected to one of the supports, termed a pilot-support, and capable of imparting thereto a rectilinear travel at constant speed between an initial position and a final position of the pilot-support in an operative travel of the film-screens assemblies in operation of the apparatus;
   a locking device having an inoperative position and an operative position in which operative position it is capable of retaining the pilot-support in said initial position;
   an actuating device controllable by the movement of the radiogenic source and cooperative with the locking device under such conditions that, at the moment when X-rays are emitted during the tomographic sweep travel, the locking device is rendered inoperative and the pilot-support is released whereby under the effect of the driving device the film-screens assemblies effect the required relative differential travels.

2. An apparatus as claimed in claim 1, wherein the driving device comprises a driving means which has a rectilinear travel which exerts on the pilot-support a force to shift the pilot-support in a direction toward said final position in an operative travel, a regulating device being combined with the driving means for ensuring that the driving means travels at constant speed.

3. An apparatus as claimed in claim 2, wherein the driving means is an extensible elastically yieldable element having one end connected to the cassette and an opposite end connected to the pilot-support.

4. An apparatus as claimed in claim 3, wherein the elastically yieldable element is a tension coil spring constantly under tension.

5. An apparatus as claimed in claim 2, wherein a flexible transmission connects the regulating device to the end of the driving means which is connected to the pilot-support.

6. An apparatus as claimed in claim 2, wherein the regulating device comprises two single-acting hydraulic jacks having rods and work chambers, two conduits disposed in parallel interconnecting the work chambers, one conduit having an adjustable constriction and the other having a check-valve which is capable of closing when the pressure is exerted in the work chamber of one of the jacks, termed a primary jack.

7. An apparatus as claimed in claim 6, wherein a flexible transmission connects the regulating device to the end of the driving means which is connected to the pilot-support and the primary jack rod is connected to the end of said transmission opposed to the end thereof connected to the driving means and cooperates with the locking device which is capable of retaining, in its operative position, said rod in an initial armed position.

8. An apparatus as claimed in claim 7, wherein, for the inoperative position of the locking device, the primary jack rod is free to put the corresponding work chamber under pressure under the effect of the pull exerted by the transmission, by closure of the check-valve and the flowing of the hydraulic liquid, in accordance with a predetermined rate of flow through the constriction, and thereby fill the work chamber of the other jack, termed secondary jack.

9. An apparatus as claimed in claim 6, wherein the constriction is adjustable by a screwthreaded rod having an end in the form of a needle valve member.

10. An apparatus as claimed in claim 6, comprising a movable locking means which is part of the actuating device for maintaining the locking device in its operative position, the lockinig device comprising two pawls which are pivotable relative to the cassette about two pivot axes and form on one side of the pivot axes branches of a jaw capable of retaining the rod of the primary jack in the initial armed position, and, on the other side of the pivot axes, define a passageway in which is engageable and from which is withdrawable the locking means for respectively precluding and allowing the opening of the jaw branches.

11. An apparatus as claimed in claim 10, wherein the pawls are subjected to an elastically yieldable means for biasing the jaw branches toward each other.

12. An apparatus as claimed in claim 11, comprising anchoring means combined with the rod of the primary jack which are cooperable with the branches of the jaw and define surfaces forming a cam adapted to move the branches away in opposition to the elastically yieldable means when the locking means is in its inoperative position under the effect of the displacement of the rod of the primary jack in either direction.

13. An apparatus as claimed in claim 6, wherein the rods of the two jacks are parallel and carry racks, and a gear pinion meshing with the two racks operatively interconnects the rods.

14. An apparatus as claimed in claim 13, wherein the pinion is integral with a rotary shaft on which there is fixed drive means for ensuring, after said operative travel of the film-screens assemblies has been effected, the return of the rod of the primary jack to the initial armed position.

15. An apparatus as claimed in claim 1, comprising a movable locking means which is part of the actuating device for maintaining the locking device in its operative position.

16. An apparatus as claimed in claim 15, comprising means for elastically biasing the locking means to an operative position of the locking means.

17. An apparatus as claimed in claim 16, comprising an elastically yieldable member constituting a withdrawable stop on the cassette for retaining the locking means in an inoperative position in opposition to said means elastically biasing the locking means and thereby permitting the return of the primary jack rod to its initial armed position, a control element cooperative with the stop to withdraw the stop at the end of the return travel being connected to the primary jack rod.

18. An apparatus as claimed in claim 15, comprising an electromagnet having a coil and plunger, the locking means being integral with the plunger of the electromagnet whose energization causes, in succession, the passage of the locking means to its inoperative position and the passage of the locking device to its inoperative position.

19. An apparatus as claimed in claim 18, wherein a circuit supplies power to the coil of the electromagnet, the circuit being adapted to be controlled by emission of the rays of the radiogenic source.

20. An apparatus as claimed in claim 1, comprising a mount for carrying the locking device, which mount is movable with respect to the cassette, and means for locking the mount in a selected given position for regulating the initial position of the pilot-support.

21. An apparatus as claimed in claim 20, comprising selecting means for controlling the movements of the mount.

22. An apparatus as claimed in claim 21, wherein the selecting means is a rack and pinion arrangement.

23. An apparatus as claimed in claim 21, wherein a brake is provided for locking the mount in the position defined by the selecting means.

* * * * *